(12) United States Patent
Berg et al.

(10) Patent No.: US 7,181,271 B2
(45) Date of Patent: Feb. 20, 2007

(54) SYNERGISM OF PHOTODYNAMIC AND ELECTROPERMEATION EFFECT ON CELL VITALITY AS A NOVEL CYTOTOXIC AGENT

(75) Inventors: Herman Berg, Jena (DE); Maya Lambreya, Sofia (BG)

(73) Assignee: Genetronics, Inc., San Diego, CA (US)

( * ) Notice: Subject to any disclaimer, the term of this patent is extended or adjusted under 35 U.S.C. 154(b) by 274 days.

(21) Appl. No.: 10/677,214

(22) Filed: Oct. 1, 2003

(65) Prior Publication Data

US 2005/0177207 A1 Aug. 11, 2005

(51) Int. Cl.
*A61N 1/30* (2006.01)

(52) U.S. Cl. .............................. 604/20; 604/500; 607/88

(58) Field of Classification Search ............ 604/20–21, 604/501, 272; 606/32–36, 27, 15–16; 607/1–3, 607/72–74, 88–94, 115–116, 120; 435/173.4–173.6; 514/947; 700/282
See application file for complete search history.

(56) References Cited

U.S. PATENT DOCUMENTS

| | | | | | |
|---|---|---|---|---|---|
| 5,079,262 | A | * | 1/1992 | Kennedy et al. | 514/561 |
| 5,474,528 | A | * | 12/1995 | Meserol | 604/20 |
| 5,674,267 | A | * | 10/1997 | Mir et al. | 607/72 |
| 6,041,252 | A | * | 3/2000 | Walker et al. | 604/20 |

* cited by examiner

*Primary Examiner*—Catherine S. Williams
(74) *Attorney, Agent, or Firm*—Daniel M. Chambers; Douglas C. Murdock; Bio Technology Law Group (57) ABSTRACT

The present invention is based on the discovery that electroporation of a photosensitive agent in a cell and subsequent activation of the agent provides more effective killing of the electroporated cell than cells exposed to a photosensitive agent alone. The invention provides a method and apparatus for inhibiting cell growth or enhancing cell death. The method includes providing a photosensitive agent to a cell; applying an electric pulse to the cell of a sufficient strength and duration to electroporate the cell with the photosensitive agent; and applying light of an activatable wavelength to the cell thereby activating the agent and inhibiting cell growth or enhancing cell death.

22 Claims, 3 Drawing Sheets

SYNERGISM OF PHOTODYNAMIC AND ELECTROPERMEATION EFFECT ON CELL VITALITY AS A NOVEL CYTOTOXIC AGENT

RELATED APPLICATIONS

Under 37 U.S.C. 119(e)(1), this application claims the benefit of prior U.S. provisional application Ser. No. 60/090,751, filed Jun. 26, 1998, which is herein incorporated by reference.

FIELD OF THE INVENTION

The present invention relates generally to electroporation and photosensitization, and more specifically to an apparatus useful for electropermeation of photosensitive agents and methods for inhibiting cell growth or enhancing cell death.

BACKGROUND OF THE INVENTION

Photoactivation or Photosensitization is a process in which a photosensitive substance activated or excited by energy provided by light or heat forms a highly reactive molecule that transfers its energy (e.g., hydrogen or electron) to other molecules during its return to the unactivated or unexcited state (decay). Transfer of hydrogen or electron to oxygen can form free radical or singlet oxygen, for example, as well as reactive decay intermediates, which subsequently react with or otherwise modify other components. Photooxidizing agents are a particular type of photosensitive agent that forms reactive molecules which oxidize components, and generally function by either of two pathways as shown below: Type (1) activated photooxidizing agent ($^3D$) reacts with oxygen (hydrogen or electron transfer) to produce a positive agent radical and free radical oxygen. The positive agent radical reacts with guanine, for example, and the free radical oxygen can react with other organic components. Type (2) activated photooxidizing agent ($^3D$) transfers energy to oxygen to produce singlet oxygen which subsequently reacts with cell components such as guanine, for example.

Type (1): $^3D+O_2$ $D^++O_2^-$ $D^++G$ $D+G^+$
Type (2): $^3D+O_2$ $D+^1O_2$ $^1O_2+G$ $O_2^-+G^+$ Where: D, $^3D$—dye and its triplet (activated or excited) state; G, $G^+$—guanine as substrate, its radical splits the DNA backbone; and $O_2$, $^1O_2$, $O_2^-$—oxygen, its single state, its radical.

Photosensitive agents have been used for killing cells since the beginning of the century. Photooxidation by natural and synthetic agents has been used experimentally for the destruction of diseased tissue and cancer (Kessel D, *Photochem. Photobiol.* 44:489 (1986); Bottiroli et al., *Photochem. Photobiol.* 47:209 (1988); G. Jori and C. Perria (eds), Photodynamic Therapy of tumors and other diseases, Libreria Progetta Editore, Padova, 1985; Berg et al., *J. Naturwiss.* 53:481 (1966); Koston et al., *J. Photochem. Photobiol.* B 36:157 (1996); Berg, H., *J. Photochem. Photobiol.* 28:399 (1988); Kennedy et al., U.S. Pat. No. 5,079,262). The photodynamic destruction (photodynamic therapy) of tumors nowadays is one of the more effective methods in cancer therapy (G. Jori and C. Perria (eds), 1985 supra; Koston et al., supra (1996)). Hyperthermia, or heat increases the reaction rate of the photooxidizing agent thereby increasing photodynamic destruction (Kimel et al., *J. Laser Surg. Med.* 12:432 (1992)). However, systemic administration of photooxidizing agents usually is associated with nonselective cell killing. Furthermore, many agents are relatively insoluble making their in vivo usefulness limited.

The cell membrane may be transiently permeabilized by subjecting cells to a brief, high intensity, electric field. This electrically-induced permeabilization of cell membranes, termed electroporation, has been used by investigators to introduce various compositions such as drugs, DNA, RNA, proteins, liposomes, latex beads, whole virus particles and other macromolecules into living mammalian cells (Berg et al., Electric field effects on biological membranes: electroincorporation and electrofusion In: Bioelectrochemistry II, Membrane Phenomena (Eds. R. G. Milazzo, M. Blank) Plenum Press, N.Y., London, p. 135–1661 (1987); Lehmann et al., *Bioelectrochem. Bioenerg.* 41:227–229 (1996); Hapala, *Crit. Rev. Biotechnol.* 17:105 (1997); Eanault et al., *Gene* 144:205 (1994); Chu et al., *Nucl. Acids Res.* 15:1311 (1987); Knutson et al., *Anal. Biochem.* 164:44 (1987); Gibson et al., *EMBO J.* 6:2457 (1987); Dower et al., *Genetic Engineering* 12:275 (1990); Mozo et al., *Plant Molecular Biology* 16:917 (1991)). These studies show that electroporation affords an efficient means to deliver therapeutic compositions such as drugs, genes, polypeptides and the like in vivo by applying an electrical pulse to particular cells, tissues or organs within a subject.

Therapeutic applications of electroporation are now being explored: introduction of functional genes for gene therapy (Nishi et al., *Cancer Research* 56:1050 (1996)); electroporation of skin for the delivery of drugs into the skin or for the transdermal delivery of drugs across tissue (Zhang et al., *Biochem. Biophys. Res. Comm.* 220:633(1996)), Weaver et al., U.S. Pat. No. 5,019,034 and Prausnitz, *Adv. Drug. Deliv.* 18:395 (1996)); angioplasty combined with electroporation to deliver drugs to a localized portion of coronary or peripheral arteries has been used to treat restenosis (Shapland et al., U.S. Pat. No. 5,498,238); cancer treatment by electroporation in the presence of low doses of chemotherapeutic drugs (Mir, U.S. Pat. No. 5,468,223). Particular apparatus for in vivo electroporation have been developed to effect treatment: Hofmann describes a syringe apparatus for electroporating molecules and macromolecules into tissue regions in vivo in which the needles of the syringe used to deliver the molecules also function as electroporation electrodes (U.S. Pat. No. 5,273,525). Weaver describes an electroporation apparatus for the delivery of chemical agents into tissues in vivo (U.S. Pat. No. 5,389,069). Hofmann et al., describe an electroporation catheter device useful for delivering genes or drugs to treat endothelial and other cells of blood vessels, for example (U.S. Pat. No. 5,507,724). Crandell et al. describe an electroporation catheter apparatus useful for introducing therapeutic macromolecules into endothelial cells of a patients blood vessels (U.S. Pat. No. 5,304,120).

Although numerous efforts have been directed to developing new therapeutic approaches to cancer treatment, cancer continues to be one of the more vexing cell proliferative disorders affecting mankind. Thus, a need exists for the development of new methods and apparatus for treating cancer and other cell proliferative disorders. The present invention satisfies this need and provides related advantages as well.

SUMMARY OF THE INVENTION

The present invention is based on the discovery that electroporation of a photosensitive agent in a cell and subsequent activation of the agent provides more effective killing of the electroporated cell than cells exposed to a photoosensitive agent alone. Thus, photosensitization and electroporation combined is an effective method for treating disorders characterized by abnormal or undesirable cell proliferation.

In a first embodiment, the invention provides a method for inhibiting cell growth or enhancing cell death. The method includes providing a photosensitive agent to a cell; applying an electric pulse to the cell of a sufficient strength and duration to electroporate the cell with the photosensitive agent; and applying light of an activatable wavelength to the cell thereby activating the agent and inhibiting cell growth or enhancing cell death.

In another embodiment, the invention provides a method for treating a cell proliferative disorder in a subject including administering a photosensitive agent to the subject having or suspected of having a cell proliferative disorder; applying an electric pulse to a cell in the subject of a sufficient strength and duration to electroporate the cell with the photosensitive agent; and applying light of an activatable wavelength to the cell thereby activating the agent and treating the cell proliferative disorder.

In one aspect, the invention provides an apparatus for treating a cell proliferative disorder in a subject. The apparatus includes an electrode capable of applying an electric pulse of sufficient strength and duration to electroporate a cell in the subject; and a light conductor for applying light of an activating wavelength to the electroporated cell.

DETAILED DESCRIPTION OF THE INVENTION

The present invention is based upon the discovery that electroporation induced introduction of a photosensitive agent into a cell (i.e. electroincorporation), followed by activation of the agent by light or heat, can inhibit cell growth or enhance cell death where the activated agent is a photooxidizing agent, for example. The invention therefore provides methods for inhibiting cell growth or for enhancing cell death as well as in vivo methods including treating a subject with a cell proliferative disorder. A method of the invention applies an electric pulse of a sufficient strength and duration to a cell to introduce a photosensitive agent, applies light of an activatable wavelength to the cell to activate the agent, whereby the activated agent inhibits cell growth or enhances cell death. In one embodiment, a method of the invention employs a photooxidizing agent which can cause oxidization of components of the electroporated cell, such as nucleic acid, thereby inhibiting cell growth or enhancing cell death. An apparatus for treating a cell proliferative disorder in a subject also is provided that includes an electrode capable of applying an electric pulse of sufficient strength and duration to electroporate a cell in the subject, and a light conductor for applying light of an activating wavelength to the electroporated cell.

The apparatus and the methods of the invention are advantageous in several respects. The apparatus and methods allow for inhibiting cell growth or enhancing cell death greater than that produced by treating cells with a photosensitive agent alone (i.e. without electroporation) or electroporation alone (without a photosensitive agent), for example. Thus, the invention can employ lower doses of a photosensitive agent than is typically used in photooxidizing treatment therapies, for example. The invention apparatus and methods are further advantageous when used in combination with other techniques for inhibiting cell growth, enhancing cell death or for treating cell proliferative disorders. For example, in a method of the invention including heat, the addition of heat promotes or accelerates diffusion of the photosensitive agent thereby providing an additive or synergistic effect. As the invention employs electroporation and photosensitive agents that are non-toxic in the unactivated state, if desired, the invention methods afford exquisite control of inhibiting cell growth or enhancing cell death of undesirable or hyperproliferative cells while avoiding surrounding healthy cells or tissue. For example, electroporating diseased tissue or hyperproliferative cells with a photosensitive agent while avoiding electroporation of non-diseased tissue or normal cells targets particular tissue or cells for death while avoiding death of normal tissue or cells. Similarly, applying light to an electroporated tumor cell population containing a photosensitive agent without applying light to non-electroporated surrounding normal tissue also minimizes cell death of non-diseased or normal tissue. Thus, the invention methods and apparatus can be used to more effectively treat a cell proliferative disorder in a subject including, for example, cancers.

The term photosensitive agent is used herein broadly to mean a molecule that is directly or indirectly toxic to cells when activated or excited by light, heat, electromagnetic or other physical, chemical (e.g., pH) or environmental stimuli capable of producing the activated or excited state. The term activated agent refers to an agent so activated or excited. Photosensitive agents include agents that are directly toxic to cells in the activated or excited state as well as agents that produce a reactive product, byproduct or intermediate that is toxic to cells upon subsequent decay of the agent from the activated to the inactivated state. For example, light activated thiopyronin is not toxic per se, but activated thiopyronin reacts with oxygen to produce toxic oxygen species (e.g., free radical oxygen). Free radical oxygen, in turn, oxidizes organic substrates, including, for example, nucleic acid, protein, lipid, carbohydrate and the like. Oxidation of a sufficient number of such cell components can inhibit cell growth or induce cell death.

Photosensitive agents typically are small molecules with ring structures although such agents can be any chemical, drug, protein, peptide, chimera or conjugate thereof so long as the molecule is directly or indirectly toxic upon activation or excitation. As used herein, the term photooxidizing agent refers to a photosensitive agent that directly or indirectly produces modification of components generally characterized by oxidation. Although photooxidizing agents such as thiopyronin, protoporphyrin and daunomycin are preferred, the invention is not to be limited to photooxidizing agents. Rather, it is specifically intended that any drug, chemical, protein etc. that is photosensitive, as set forth herein, which directly or indirectly produces modifications of components, a sufficient number of which can inhibit cell growth or induce cell death, is included. For example, a photosensitive agent, upon activation, may directly or indirectly reduce components and therefore could be referred to as a photoreducing agent. A photosensitive apoptotic protein or peptide (e.g., fas) or conjugate, upon activation, would directly or indirectly induce or enhance cell apoptosis and therefore could be referred to as a photoapoptotic agent. Thus, photosensitive agents that directly or indirectly modify components in a variety of different ways are included.

As used herein, the term component means a substance or molecule in a cell that can be directly or indirectly modified by the activated or excited photosensitive agent, or a reactive product, byproduct or intermediate produced by the activated agent or its decay. Generally, modifiable components are nucleic acid, protein, lipid, carbohydrate, small organic molecules (e.g., steroid hormones) and other substances that are present naturally in cells. However, components can be non-naturally occurring substances that, when introduced into the cell, are modified as set forth herein by a photosensitive agent, such modification subsequently inhibiting cell growth or enhancing cell death. When a sufficient number of the naturally or non-naturally occurring modified components accumulate, cell growth can be inhibited or cell death can be enhanced.

The photosensitive agents useful in practicing the invention methods and with the invention apparatus can be relatively non-toxic or toxic (i.e. cytostatic). Specific photosensitive agents include, for example, thiopyronin, acridine orange, Zn-phthalocyanine-sulfonate, benzoporphyrin, protoporphyrin, hematoporphyrin, PHOTOFRIN I, PHOTOFRIN II, ANTRIN, porphycene and functional derivatives thereof. Specific cytostatic agents include, for example daunomycin, adriamycins and actinomycins, anthranycins, mitomycins, phenylazides, chromomycin A, methylene blue and mitramycin A.

Additional photosensitive agents include PHOTOFRIL, organic dyes, Monostral Fast Blue, synthetic diporphyrins and dichlorins, hydroporphyrins such as chlorins and bacteriochlorins of the tetra(hydroxyphenyl)porphyrin series, phthalocyanines, O-substituted tetraphenyl porphyrins, 3,1-meso tetrakis(-propionamido phenyl)porphyrin, verdins, purpurins, tin and zinc derivatives of octaethylpurpurin (NT2), etiopurpurin (ET2), chlorins, chlorin e6, mono-1-aspartyl derivative of chlorin e6, benzoporphyrin derivatives (BPD), benzoporphyrin monoacid derivatives, tetracyanoethylene adducts of benzoporphyrin, dimethyl acetylenedicarboxylate adducts of benzoporphyrin, Diels-Adler adducts of benzoporphyrin, monoacid ring a derivative of benzoporphyrin, sulfonation of aluminum PC as sulfonated AlPc, disulfonated ($AlPcS_2$), tetrasulfonated derivative, sulfonated aluminum naphthalocyanines, zinc naphthalocyanines, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide, hematoporphyrin (HP), protoporphyrin, boronated porphyrins, and adducts of suitable sensitizers with antibodies.

Other photosensitive agents that can be used in the invention can be found, for example, in Thompson et al. (U.S. Pat. No. 5,277,913) and in Hearst et al. (U.S. Pat. No. 5,503,721), which are incorporated herein by reference.

Additional compositions useful in practicing the methods of the invention include visualizing agents, such as 5-amino laevulinic acid, which emits fluorescence, and is therefore useful for visualizing the target site. Thus, in another embodiment, a method of the invention includes administering a visualizing agent to the subject.

Modified or derivatized compositions that are functional analogues of the photosensitive agents described herein and known in the art also are useful in the methods of the invention. Such modified compositions can have sulfate groups, phosphate groups, or hydrophobic groups such as aliphatic or aromatic chemical moieties added or removed, or can have additional functional moieties conjugated thereto (e.g., biotin, streptavidin, polyhistidine etc.). Functional conjugates of photosensitive agents also can be used.

As used herein, the terms impulse, pulse, electrical impulse, electrical pulse, electric pulse, electropulse and grammatical variations thereof are interchangeable and all refer to an electrical stimulus. Although the various terms are frequently used herein in the singular and plural, the use of either form is not intended to exclude the other (i.e., reference to multiple pulses includes a single pulse and vice versa). Preferred electric impulses are pulsed electric fields such as those applied via an electroporation apparatus, for example. It is understood that electroporation of a normal or diseased cell, tissue, or organ can be performed in vitro, in vivo, or ex vivo. Electroporation can also be performed utilizing single cells, e.g., single cell suspensions or in vitro or ex vivo, optionally in cell culture.

Suitable electric pulses for electroporating a cell with a photosensitive agent include, for example, square wave pulses, exponential waves, unipolar oscillating wave forms, bipolar oscillating wave forms, other wave forms generating electric fields, or a combination thereof. Each pulse wave form has particular advantages; square wave form pulses provide increased cell transformation efficiencies in comparison to exponential decay wave form pulses, and the ease of optimization over a broad range of voltages, for example (Saunders, Guide to Electroporation and Electrofusion, 1991, pp.227–47). Preferably, the waveform is a square wave pulse.

The electric pulse can be provided by any electronic device that provides an appropriate electric pulse. Exemplary pulse generators capable of generating a pulsed electric field include, for example, the ECM600, which can generate an exponential wave form, and the ElectroSquarePorator (T820), which can generate a square wave form, both of which are available from BTX, a division of Genetronics, Inc. (San Diego, Calif.). Additional electroporation type apparatus are commercially available and it is understood that such apparatus can be used to generate the pulse for practicing the invention methods. Moreover, the ECM600, the ElectroSquarePorator (T820) and other such apparatus can be used to provide the electric pulse to the pulse applicator of the invention apparatus, as set forth herein.

The pulse strength for electroporation will range from about 25 to about 200 volts, preferably from about 40 to about 100 volts and more preferably from about 50 to about 80 volts. Generally, the field strength, which is calculated by dividing the voltage by the distance between the electrodes (V/d, where d is generally in cm), will generally be from about 10 volts/cm to about 6.0 kV/cm. The pulse width or duration generally will be from about 100 microseconds (s) to 50 milliseconds (ms), preferably from about 100 s to about 25 ms and more preferably from about 100 s to 10 ms. The capacitance will generally range from about 100 to about 1000 F, preferably from about 200 to about 800 F, more preferably from about 400 to about 800 F. There can be from about 1 to about 100 pulses applied. Preferably, the number of pulses is from about 1 to about 50 pulses and more preferably from about 1 to about 20 pulses. Most preferably, 1 to 10 pulses are applied. The various pulse parameters (e.g., voltage, field strength, waveform type, duration, capacitance and the number of pulses applied) for electroporating cells in vivo can be found in a database maintained by GENETRONICS, INC., (San Diego, Calif.). The electric fields needed for in vivo cell electroporation, are generally similar in magnitude to the fields required for cells in vitro; the preferred magnitudes are in the range of from about 10 V/cm to 6000 V/cm; from about 10 V/cm to 2000 V/cm; or about 100 V/cm to 1500 V/cm. In vivo electropulsing parameters for tumors and other tissues using a needle electrode apparatus are described in copending application Ser. No. 09/177,678, which is a continuation in part of application Ser. No. 08/905,240, both of which are herein incorporated by reference.

Light can be applied prior to, during or after electroporation using a variety of light sources, so long as the light is of an appropriate wavelength and is of sufficient energy to activate the photosensitive agent. Activation of a photosensitive agent by light generally depends upon the absorption spectrum of the agent which depends on the chemical composition, structure, chirality, conformation etc. of the agent. The amount of excited sensitizer concentration depends on the amount of absorbed photons. For example, thiopyronin has an absorption maximum of 560 nm, protoporphyrin has an absorption maximum of 370 nm and at 630 nm, daunomycin has an absorption maximum 480 nm and therefore, light of a wavelength that corresponds to the absorption maximums is appropriate for activation. In contrast, porphycenes are activated by light of longer wavelengths, between about 650 and 950 nm. Thus, broad band light having a wavelength from about 300 to about 950 nm can be used to generally activate any photosensitive agent that has an absorption maximum within the wavelength of the broad band light (i.e. within 300 to 950 nm).

As an alternative to applying broad band light, light of a narrower wavelength that is at or near the absorption maximum of the particular agent can be applied to the agent to activate the agent, if desired. As light induced activation of a photosensitive agent can increase by increasing the energy of light applied to the agent or decrease by decreasing the energy of light applied to the agent, the energy of light applied (Joules/cm$^2$) can be varied so as to regulate activation of the photosensitive agent, if desired.

Suitable light sources that can be used to apply light of an activatable wavelength include tungsten lamps, lasers, various fiberoptics and arthroscopic instruments, for example. The selection of the light source will depend on the particular application or the particular cell proliferative disorder treated. For example, in a method of the invention practiced extracorporeally, the light source can be a tungsten lamp or laser. In a method of the invention in which light is applied internally (i.e. within a subject), the light source can be applied by a fiberoptic rod, which can be passed into the target site via an arthroscope or other similar device. A fiberoptic rod can optionally comprise a plurality of optic fibers, which can be passed into a target site via a small hollow tube such as a hypodermic needle, for example.

Certain wavelengths of light are more effective at penetrating skin or into deeper tissues. For example, wavelengths at or above about 400 nm begin to penetrate skin; higher wavelengths penetrate skin to greater depths. Thus, an external light source that applies light having a wavelength greater than about 400 nm can be used to activate a photosensitive agent electroporated into a cell population in an internal space, tissue or organ. However, because certain light wavelengths (e.g., UV of about 290–320 nm) have deleterious effects on normal cells, tissues or organs, it is important that the light sensitivity of normal tissue be taken into consideration. Thus, appropriate shielding can be used if necessary to protect skin, tissues or organs from light. Alternatively, light sources that apply light of an appropriate narrow wavelength range (e.g., 650 to 750 nm) can be used to activate a photosensitive agent (e.g., porphycenes) while minimizing deleterious side effects produced by light wavelengths outside the particular range.

Thus, the wavelength, energy and the amount of time the light is applied to activate the electroporated photosensitive agent will therefore depend on the agent, the subject and the nature of the cell proliferative disorder. In general, the energy applied will be from about 50 to about 1000 J/cm$^2$, preferably from about 100 to about 500 J/cm$^2$. The time the light is applied will range from about 10 seconds to about 4 hours, preferably from about 1 min to about 2 hours, more preferably from about 5 min to about 1 hour and most preferably from about 10 min to 30 min. Nevertheless, the skilled artisan will recognize that light can be applied for significantly longer periods of time, for example, where visible light activates the agent, such as an agent applied topically to the skin, mere exposure to sunlight or indoor light can result in light of an activatable wavelength being applied for much longer.

The diffusion of photosensitive agents into cells that occurs upon electroporation may be accelerated by heat. Thus, in another embodiment, heat can be applied prior to, simultaneously with or after applying an electric pulse, in lieu of applying light, in addition to applying light, or at any time between electric pulsing and applying light of an activatable wavelength in a method of the invention. Heat can be provided by placing a typical electrical heating element within an electrode, such as a needle electrode, and applying the heated electrode to the cell, prior to or after electroporation. Alternatively, heat can be provided by a heating element or by microwave energy, for example, by an external heat source. Heat also can be provided by a light source, as with a tungsten lamp, or laser, for example. The temperature of heat applied will be at least 1 C greater than ambient temperature or, where heat is applied in a method of the invention practiced on a subject, at least 1 C greater than the temperature of the cells, tissue or organ of the subject to which the heat is being applied. Thus, the temperature of the heat applied will range from about 18 C to about 50 C (e.g., for local treatment). Preferably, the temperature of the heat applied will be from about 25 C to about 45 C, more preferably from about 36 C to about 42 C. The particular temperature of the heat applied will depend on the cells, tissues treated, whether the cells are treated in vitro or in vivo, the photosensitive agent used and the desired therapeutic effect.

In the absence of light or other comparable activating phenomenon, photosensitive agents are preferably relatively non toxic to cells; their toxicity depends upon activation or subsequent decay of the activated state, as set forth herein. Nevertheless, photosensitive agents include drugs, chemicals and other substances that are already be toxic or reactive, which can be made further or differently reactive or toxic when activated or excited by light, heat etc. For example, particular chemotherapeutic agents, which are inherently cytotoxic, such as daunomycin, can acquire greater cytotoxicity or be made more cytotoxic by exposure to light than in their unactivated or unexcited state (Example I and FIG. 3).

As used herein the term cytotoxic or cytotoxicity refers to toxicity towards cells, tissues, organs or a subject. Toxicity can be quantitated in cells or in animals as the amount of an agent needed to induce 50% cell death (i.e., $ED_{50}$), for example, or by other methods well known in the art.

Photosensitive agents used in a method of the invention can be administered by any appropriate mode. Appropriate modes of administration include, for example, by injection intravenously, intraperitoneally, intramuscularly, subcutaneously, intraspinally, intracranially, intracavity etc. Modes of administration further include oral (in pill, liquid or powder), intravaginal, rectal (e.g., suppository), buccal, intraoccullar, intranasal, topical (e.g., by spreading or by a drug impregnated patch), inhalation (e.g., by an aerosol or other misting device). The term topical is used herein to refer to administration of a composition on the surface of the skin or mucosa. The compositions can be administered as a bolus, by gradual perfusion over time or by an implantable drug delivery device which can release a user definable quantity of drug, for example.

Photosensitive agents, when administered in a method of the invention, will generally be in pharmaceutically acceptable or physiologically acceptable formulation for therapeutic use. As used herein, the terms pharmaceutically acceptable and physiologically acceptable refer to carriers, diluents, excipients and the like that can be administered to a subject, preferably without excessive adverse side effects (e.g., headache, stomach upset etc.). Particular formulations include aqueous or non-aqueous solutions, suspensions, emulsions, oils or other liquid formulations suitable for the modes of administration described herein and further known in the art. Such formulations are compatible or are inert with respect to the photosensitive agent, and its ability to be activated as set forth herein. Examples of non-aqueous solvents are propylene glycol, polyethylene glycol (PEG) in its various molecular weights (e.g., PEG 400, PEG 400 monostearate, PEG 4000 etc.), glycerine, polyvinyl pyrrolidine (PVP), polyvinyl alcohol (PVA), mannitol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives, and other additives may also be present such as, for example, antimicrobial, chelating agents (e.g. EDTA, EGTA), and inert gases and the like. It is also possible to entrap a photosensitive agent into micro-capsules prepared by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, and lipid-based systems including oil-in-water emulsions, micelles, mixed micelles, and liposomes. The preparation of an appropriate pharmaceutical formulation for therapeutic use is well within the general knowledge in the art (see e.g., Remington s Pharmaceutical Sciences, supra, 1997)

A permeation enhancer also can be included with the formulation to increase electroporation of the photosensitive agent into the cell. As used herein, the term permeation enhancer refers to any action (e.g., mechanical, physical) or any composition that can increase or augment electroporation. The term augment, when used herein as a modifier of electroporation, means that the rate (over time) or amount of composition electroporated into cells is greater than that produced by electroporation in the absence of the permeation enhancer. Thus, a permeation enhancer can be mixed with the photosensitive agent in a pharmaceutical formulation, for example, to increase electroporation of the photosensitive agent. Permeation enhancer compositions that increase cell permeability include, for example, alcohols (e.g., methanol), alkyl methyl sulfoxides (e.g., DMSO), pyrrolidones (e.g., 2-pyrrolidone), surfactants, urea, glycerol monolaurate, polyethylene glycol monolaurate, glycerol monolaurate, docainehydrochloride, hydrocortisone, menthol, methyl salicylate and the like.

The photosensitive agents will be electroporated into a cell in an amount such that when activated or excited, the activated agent is sufficient for inhibiting cell growth or enhancing cell death. Such amounts also are considered to be an effective amount for treating a cell proliferative disorder in a subject when a desired therapeutic effect is produced, e.g., cell proliferation is inhibited, tumor cell growth is inhibited, tumor cell death is enhanced etc. Thus, an effective amount means an amount of agent that is sufficient to reduce the severity or ameliorate the signs or symptoms of the clinical situation (e.g., tumor growth is inhibited). The amount should not be so large as to cause excess adverse side effects resulting from inhibiting normal cell growth or enhancing normal cell death. The amount required will vary depending on the photosensitive agent used, cell type treated, the proliferative disorder treated, the severity of the disorder being treated, the efficiency of cell electroporation, the subject treated, the species, age, general condition of the subject and the mode of administration of the agent etc. Thus, although it is not possible to specify an exact effective amount, an appropriate effective amount in an individual case may be determined using the general teachings available in the art relating to doses of photooxidizing drugs used for solid tumor treatment, for example (see e.g., Remington s Pharmaceutical Sciences, 18th ed., Mack Publishing Co., Easton, Pa., 1990; The Merck Index, 12th ed., Merck Publishing Group, Whitehouse, N.J., 1996, which are herein incorporated by reference).

The above-described photosensitive agents and others not specifically described herein are useful in various clinical situations characterized by abnormal or undesirable cell proliferation and can be administered alone, in combination with each other, or in a combination with various other compositions and methods for treating a cell proliferative disorder in a method of the invention. For example, electroporation of two or more photosensitive agents can produce an additive or synergistic effect in comparison to electroporating one agent. One may utilize such agents as acridine orange (450 nm), thiopyronine (560 nm) and methylene blue (650 nm) in various combinations. Similarly, electroporation of a photosensitive agent in combination with an antineoplastic drug or radiation can produce an additive or synergistic effect in comparison to either electroporating the photosensitive agent or treating with the antineoplastic drug or radiation alone. Particular antineoplastic drugs that can be administered in such a method of the invention include, for example, bleomycin, neocarcinostatin, suramin, doxorubicin, carboplatin, taxol, mitomycin C and cisplatin. Other chemotherapeutic agents will be known to those of skill in the art and can similarly be employed (see e.g., Bayley et al., U.S. Pat. No. 5,777,078;

and Malpas J. S., Chemotherapy In: Introduction to the Cellular and Molecular Biology of Cancer, L. M. Franks and N Teich (eds), Oxford Science Publications, Oxford University Press, New York, pp. 363–377 (1986), which are herein incorporated by reference). The invention methods can similarly be employed in combination with surgical recission of a benign growth or a solid tumor.

The methods of the invention for inhibiting cell growth or for enhancing cell death set forth herein can be practiced in a subject, preferably a mammalian subject (e.g., those typically used in the laboratory, such as simian, rabbit, guinea pig, rat, mouse; livestock such as pig, cow, sheep, horse; domesticated animals such as dog, cat, ferrets), more preferably a human subject.

Thus, in another embodiment, the invention provides methods for treating a cell proliferative disorder in a subject. A method of the invention is practiced by administering a photosensitive agent to the subject having or suspected of having a cell proliferative disorder; applying an electric pulse to at least one cell in the subject of a sufficient strength and duration to electroporate the cell with the photosensitive agent; and applying light of an activatable wavelength to the cell thereby activating the agent and treating the cell proliferative disorder.

Various cell proliferative disorders are contemplated for treatment in a method of the invention. For example, benign cell proliferative disorders, such as autoimmune disorders (e.g., lupus, rheumatoid arthritis etc.) nodules, fibrotic growths, cysts, occlusions, psoriasis (e.g., 1 mg/kg) and the like can be so treated. Additional cell proliferative disorders suitable for treatment include cancer, such as skin cancers, solid tumors, hematopoietic cancers (e.g., histiocytic lymphoma, myelomas, leukemias), that are metastasizing or non-metastasizing. Specific cancers include lung, brain, head and neck tumors, stomach, bladder, liver, pancreas, kidney, colon, breast, uterine, ovarian, prostate and testicular cancers.

A method of the invention for treating a cell proliferative disorder in a subject can utilize a variety of devices. For example, an electroporation catheter, such as that described in application Ser. No. 08/668,725, which is herein incorporated by reference, can be used in practicing the invention methods. Additionally, the apparatus of the invention can be used to practice the methods of the invention. The apparatus comprises an electrode capable of applying an electric pulse of sufficient strength and duration to electroporate a cell in the subject, and a light conductor for applying light of an activating wavelength to the electroporated cell.

An electrode of the apparatus, operatively linked to a DC voltage source, will apply an electric pulse. A light conductor, operatively linked to a light source, will be in a position with respect to an invention electrode which enables applying light to the electroporated cell. Cells, tissue or an organ electroporated with a pulse emanating from an electrode is exposed to light emanating from a light conductor thereby activating the photosensitive agent. Thus, a compositions, such as a photosensitive agent is administered to a diseased tissue, organ or tumor, a pulse is applied with the electrode in or on the tissue, thus electroporating the cells of the tissue organ or tumor. Light is applied at some point in time prior to, simultaneously with or after applying the pulse thereby activating the photosensitive agent.

As used herein, the terms operatively linked or operatively connected or grammatical variations thereof refers to the relationship between two or more elements that allows the elements to function together in their intended manner. Thus, two or more operatively linked or operatively connected elements may be physically connected in close association, but are not required to be so connected. For example, an electrode operatively linked to a DC voltage source are connected in such a way as to allow the pulse provided by the DC voltage source to be delivered to the electrode for applying to the cell. A light conductor operatively linked to a light source is connected in such a way as to allow the light provided by the source to be delivered to the light conductor for applying to the electroporated cell.

Various embodiments of an invention apparatus are included herein. For example, as light of various wavelengths (i.e. from about 300 nm to about 950 nm) can activate a photosensitive agent, various light conductors are contemplated. In one embodiment, the light conductor applies light provided by a laser. In another embodiment, the light conductor is a laser. In yet another embodiment, the light conductor applies light provided by a visible wavelength emitter, such as that provided by a tungsten lamp. In still yet another embodiment, the light conductor is a visible wavelength light emitter or a xenon-high pressure lamp with a UV-filter or a mercury-pressure lamp with UV filter.

The light conductors can be selected or modified so as to be useful for applying light internally. Thus, in one embodiment, the light conductor comprises a fiberoptic rod. Light from a light source is transmitted through the fiberoptic rod (e.g., laser or visible light emitter). Suitable fiberoptic rods and other endoscopic light devices made of biologically compatible or inert materials, such rods and devices having a wide variety of sizes and configurations, are commercially available. Any such rod can be employed in an apparatus of the invention so long as the light applied is of an activating wavelength. The fiberoptic rods can be modified to be flexible to allow for the smooth passage through organs, tissues, vessels and the like. The fiberoptic rods also can be modified to electrically conductive so as to function as an electrode. For example, in one embodiment, a fiberoptic rod has a metallic grid on the exterior surface which can apply an appropriate electric pulse as well as allow light to pass through the grid pattern. In another embodiment, a fiberoptic rod has a metallic film deposited on the exterior surface, again so as to function as an electrode, the metallic film preferably optically transparent so as to permit light to pass through.

In another embodiment, the fiberoptic rod comprises a plurality of optical fibers. As used herein, the term plurality refers to two or more.

Various embodiments of the invention apparatus with respect to electrode types and configurations also are contemplated. In one embodiment, the apparatus includes at least two needle electrodes, one of which optionally is hollow which can be useful for providing a composition (e.g., a photosensitive agent in a pharmaceutically acceptable formulation) to the cell. The contemplated arrangement of a hollow needle electrode and a light source is similar to a laparoscopic needle array in which the needles that function for injection of therapeutic substances into tissue also function as electrodes for electroporation for portion of cells or tissue in vivo, and a light source is used for endoscopic examination, as described in application Ser. No. 09/177,678, which is a continuation in part of application Ser. No. 08/905,240, which are herein incorporated by reference. The needle-light conductor works with high intensity, diffuse and scattered light to illuminate the entire tumor, for which purpose the light conductor is shorter than the needles. U.S. Pat. No. 5,273,525, describes a syringe for injecting molecules and macromolecules and for electroporation in which needles for injection also function as electrodes. Such devices can be modified as set forth herein and connected to a light conductor (e.g., a laser) using the knowledge generally available in the art.

In another embodiment, the invention provides an apparatus in which the needle electrodes are further extended with one or more fiberoptics comprising the light conductor.

In an alternative embodiment, one or more fiberoptics are located between two needle electrodes. In either embodiment, the electrode/fiberoptic configuration is such that the tissue to be electroporated can be viewed using illumination provided by the fiberoptic while the tips of the electrode needles are inserted into the tissue or organ for subsequent electroporation. Fiberoptics of various sizes can be employed which are compatible with needle electrodes. For example, a 400 micron fiberoptic can fit within a 23 gauge needle. In another preferred embodiment, an invention apparatus has at least one heatable electrode, optionally modified as set forth herein in respect to the various embodiments of an electrode. Additional variations or modifications of the invention apparatus will be apparent to the skilled artisan and are also therefore included. Besides needle electrodes, also flexible meander electrodes are important for surface tumors (e.g., necrosis) with square dimensions. In this case, sensitizers are included in liposomes between the flat electrodes before pulsing. The irradiation takes place directly from the back-side through the slide without any light conductor.

The following examples are intended to illustrate but not limit the invention. While they are typical of those that might be used, other procedures and applications of the invention methods known to those skilled in the art may alternatively be used.

al., *Bioelectrochem. Bioenerg.* 16:135–148 (1986)). The photosensitive agents are stable during irradiation in water solution. Approximately 200 l or 400 l of a U937 cell suspension ($10^6$–$10^7$ cells/ml) in the presence of 20 l and 40 l of the photosensitive agent ($1\times10^{-5}$ M), respectively, were placed in a disposable cuvette with embedded aluminum electrodes separated by 0.2 cm. The mixture of U937 cells and photosensitive agent were subjected to a single pulse at 250 V (equivalent to a field strength of 1.2 kV/cm), 400 F, pulse width 11–12 ms, exponentially decaying pulse, applied with a BTX ECM-600.

The electropulsed and control (unpulsed) cuvettes were positioned on both sides by 650 Watt tungsten lamps (Narva, Berlin, maximum of emission at 900 nm or the Osram point lamp, 250 Watt) at 37-cm distance in the focus areas of two identical lenses, and then irradiated for 14 min. In this way, we have two identical light beams for the pulsed and unpulsed control. There are two water chambers, 4 cm thick, between the lamp and the lenses for heat absorption. Studies were carried out at ambient temperature (18–22 C).

Cell viability after irradiation (with and without electroporation) was determined by trypan blue exclusion; colored dead cells were counted in relation to uncolored cells as well as in the control solution without pulse treatment. Cells were visualized with an inverted video-microscope (Olympus, Japan). The results of these studies for U937 cells are shown in Table 1 below:

TABLE 1

|  | TP ($1 \times 10^{-5}$ M) | SD % | PP ($1 \times 10^{-5}$ M) | SD % | DAM ($1 \times 10^{-5}$ M) | SD % |
|---|---|---|---|---|---|---|
| Dead cells by pulse | 80.3 | 7.45 | 65.8 | 3.31 | 63.4 | 2.54 |
| Dead cells by light for control | 20.1 | 1.58 | 18.8 | 2.27 | 17.6 | 4.79 |
| Total dead cells for exp. | 98.6 | 1.24 | 91.6 | 4.36 | 87.5 | 0.63 |
| Final dead cells: exp/control | 4.9 |  | 4.9 |  | 4.9 |  |

EXAMPLE I

This example shows that electroporating cells with a photosensitive agent (thiopyronin, protoporphyrin and daunomycin) and subsequent irradiation of the cells produces greater cell killing than treating cells with the photosensitive agent and subsequent irradiation alone (i.e. without electroporation).

The cells were grown in RPMI 1649 medium (Sigma Aldrich) in physiological NaCl concentration or 0.6 M mannitol supplemented with 10% fetal calf serum (BIO Whittaker), 100 g/ml streptomycin (PAA, Marburg) and 1000 U/ml penicillin (PAA, Marburg) at 37 C in 5% $CO_2$ incubator of 90% humidity.

The photosensitive agents tested were thiopyronin (TP; Merck, absorption maximum 560 nm), which reacts mainly according type 1, oxidizing guanosine with the rate constant $3.8\times10^6$ 1/Ms (Goilmick et al., *J. Photochem. Photobiol.* (in German), 16:447–453 (1972)) protoporphyrin (PP; Sigma, absorption maximum 370 nm), a therapeutically important photosensitizer (Woodburn et al., *Br. J. Cancer* 65:321–328 (1992)) which reacts mainly according type 2; and daunomycin (DAM; ZIMET, Jena, absorption maximum 480 nm) an antineoplastic drug that reacts mainly according to type 1 which also shows a cytostatic activity in the dark (Berg et As shown in Table 1, electroporating cells with a photosensitive agent and subsequent light irradiation produces significantly greater cell killing than irradiation alone.

Without the water-glass filter to absorb the heat generated by the tungsten lamp, the temperature of the cell suspension rises from about 22 C to about 37 C during the 14 min irradiation and the cell killing increases by an additional 14%. The results for electroporated U937 cells irradiated for shorter periods of time (less than 14 min.) were more pronounced as the exp./control ratio is higher. Penetration and, as expected, dark effect of daunomycin (without irradiation) also increases with time for unpulsed cells. MCE-7 breast cancer cells examined in a similar photosensitivity assay displayed the same combined effect of electroporation and irradiation as with the U937 cells. We observed similar data for MCF7 and K562 cells.

EXAMPLE II

This example shows that electroporating cells with a photosensitive agent (thiopyronin, protoporphyrin and daunomycin) and subsequent irradiation for increased amounts of time produces increased cell killing.

Figure 1:
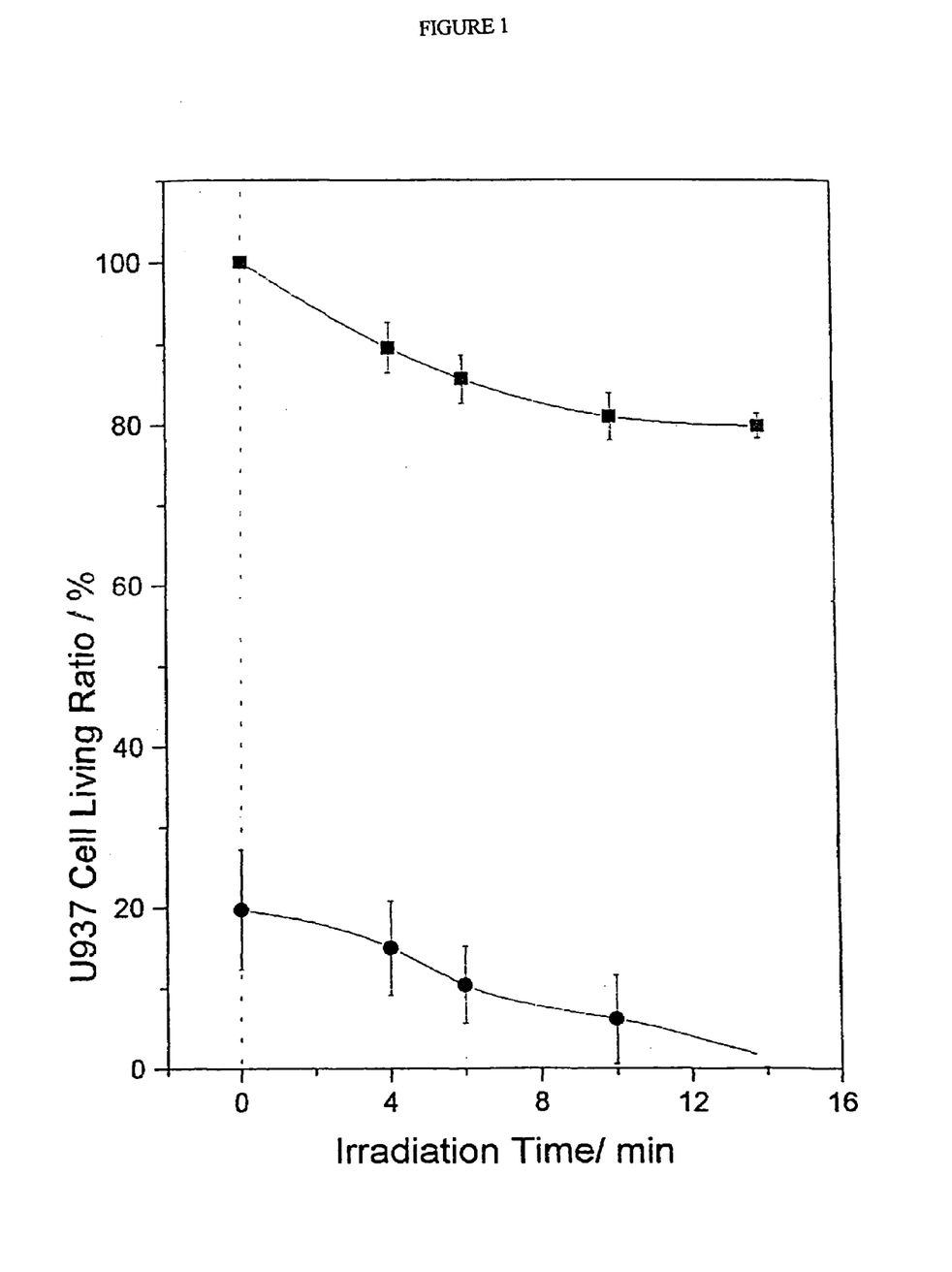
FIG. 1 shows the percentage of living U937 cells after electroporating thiopyronin ($1 \times 10^{-5}$M) and irradiating the cells (10 J/cm2 or more) for the indicated times beginning 30 seconds after the pulse (field strength 2 kV/cm, capacitance 800 F, pulse length 11–12 ms; lower curve) and irradiation only (upper curve). U937 cells were in 1:1 nutrition medium and 0.6 M mannitol, at an ambient temperature (about 18–22 C).
Figure 2:
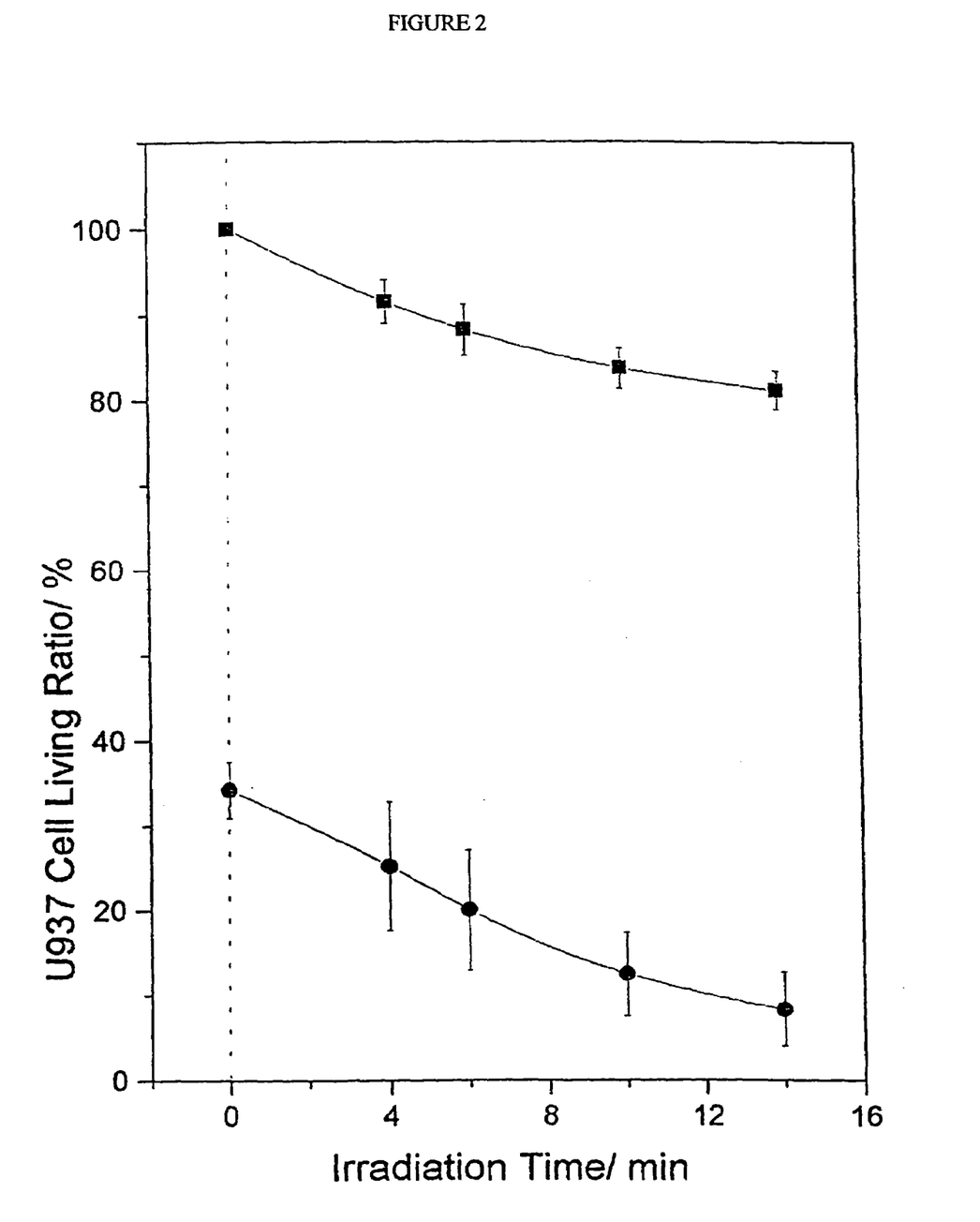
FIG. 2 shows the percentage of living U937 cells after electroporating protoporphyrin ($1 \times 10^{-5}$M) and irradiating the cells for the indicated times beginning 30 seconds after the pulse (lower curve) and irradiation only (upper curve). Pulse parameters, growth media and temperature were as before.
Figure 3:
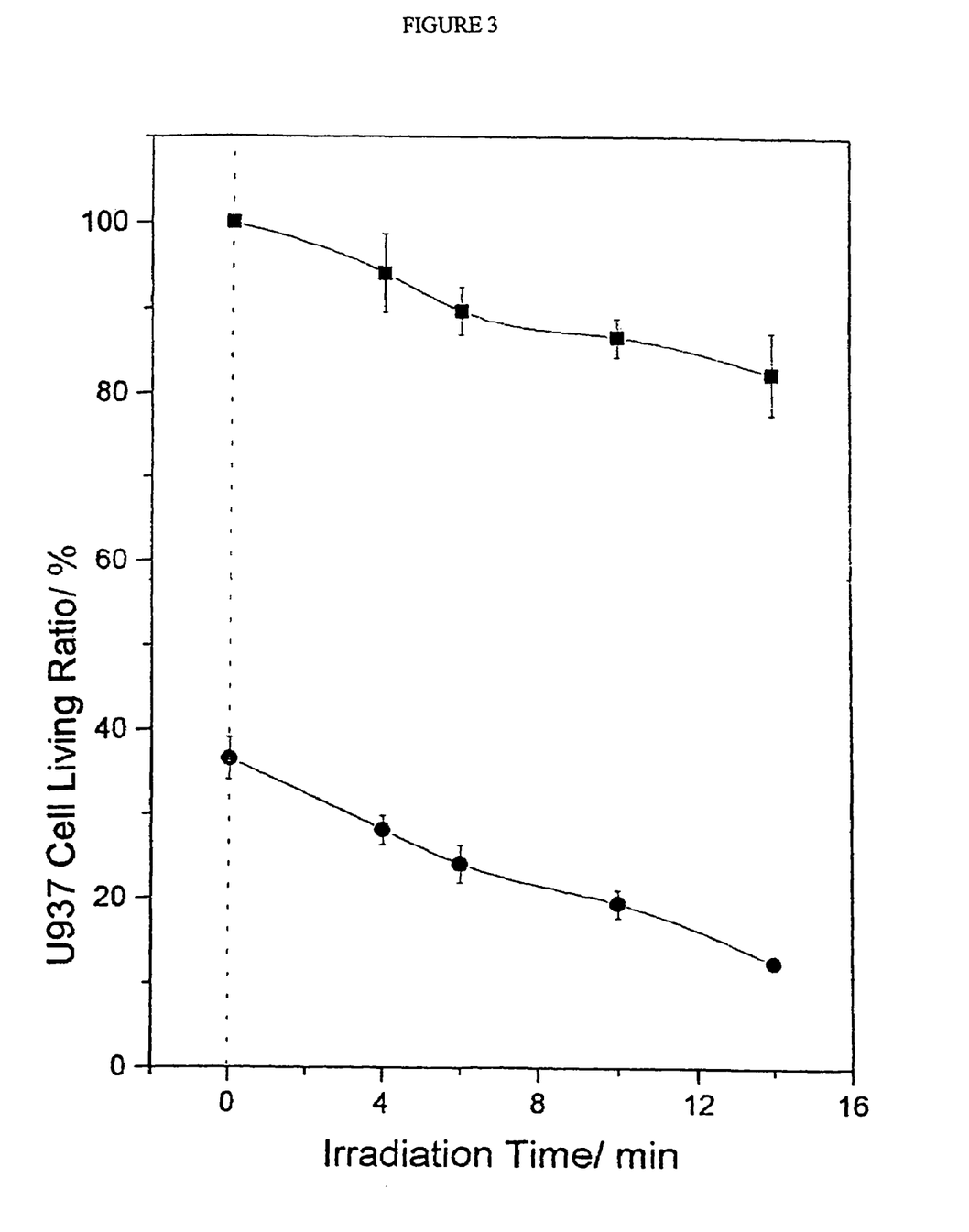
FIG. 3 shows the percentage of living U937 cells after electroporating daunomycin ($1 \times 10^{-5}$M) and irradiating the cells for the indicated times beginning 30 seconds after the pulse (lower curve) and irradiation only (upper curve). Pulse parameters, growth media and temperature were as before.

Additional studies of electroporation and cell killing were performed as above except that a higher pulse amplitude of 400 V with an 800 F capacitance (equivalent to a filed strength of 2 kV/cm) was used for electroporation. Pulsed or unpulsed cells were irradiated and, every 2–4 min afterwards, a 20 l aliquot of the irradiated cells was removed and mixed with 20 l trypan blue to determine viability as before. As shown in FIGS. 1 to 3, about 90 to 98% of cells were killed be electroporating with thiopyronin, protoporphyrin and daunomycin, respectively, and subsequent irradiation.

It will be apparent to those skilled in the art that various modifications and variations can be made to the compounds and processes of this invention. Thus, it is intended that the present invention cover such modifications and variations, provided they come within the scope of the appended claims and their equivalents. Accordingly, the invention is limited only by the following claims.

What is claimed is:

1. A method for inhibiting cell growth or enhancing cell death comprising:
   a) providing a photosensitive agent to a cell, wherein photosensitive agent is delivered as part of a pharmaceutically acceptable formulation that further comprises a pharmaceutically acceptable carrier and does not include liposomes;
   b) applying an electric pulse to the cell of a sufficient strength and duration to electroporate the cell with the photosensitive agent; and
   c) applying light of an activatable wavelength to the cell thereby activating the agent and inhibiting cell growth or enhancing cell death.

2. A method according to claim 1, wherein multiple pulses are applied to the cell.

3. A method according to claim 1, wherein the pulse amplitude is about 8410 kV/cm to about 6.0 kV/cm.

4. A method according to claim 1, wherein the pulse width is about 0.1 milliseconds to about 10 milliseconds.

5. A method according to claim 1, wherein the pulse is applied using at least two electrodes.

6. A method according to claim 5, wherein at least one light conductor is combined with the electrode.

7. A method according to claim 6, wherein the electrodes comprise at least two needle electrodes.

8. A method according to claim 7, wherein the needle electrodes are heatable.

9. A method according to claim 1, wherein the light is applied prior to, simultaneously with, or following the pulse.

10. A method according claim 1, wherein the light is applied by a laser.

11. A method according to claim 1, wherein the light is applied by a tungsten lamp.

12. The method at A method according to claim 1, wherein the light is applied by a near ultraviolet lamp.

13. A method according to claim 1, wherein the light has a wavelength of about 300 nm to about 950 nm.

14. A method according to claim 4, wherein the amount of light applied is about 50 J/cm2 to about 1000 J/cm2.

15. A method according to claim 1, wherein the light is applied extracorporeally.

16. A method according to claim 1, wherein the photosensitive agent is a cytostatic agent.

17. A method according to claim 16, wherein the cytostatic agent is selected from the group consisting of daunomycin, adriamycin and actinomycin.

18. A method according to claim 16, wherein the photosensitive agent is 1 aevuline acid.

19. A method according to claim 18, wherein the photosensitive agent is protoporphyrin IX.

20. A method according to claim 1, wherein the method is performed in a subject.

21. A method according to claim 20, wherein the subject is a human.

22. A method according to claim 1, wherein the electrodes comprise meander electrodes.

* * * * *